United States Patent
Wu et al.

(10) Patent No.: US 10,927,321 B2
(45) Date of Patent: Feb. 23, 2021

(54) TRACTION FLUID WITH IMPROVED LOW TEMPERATURE PROPERTIES

(71) Applicant: VALVOLINE LICENSING AND INTELLECTUAL PROPERTY LLC, Lexington, KY (US)

(72) Inventors: Gefei Wu, Lexington, KY (US); Rajkumar Rajule, Kalyan West (IN); Ning Ren, Naperville, IL (US); Jesse Dambacher, Lexington, KY (US); Frances Lockwood, Georgetown, KY (US)

(73) Assignee: VALVOLINE LICENSING AND INTELLECTUAL PROPERTY LLC, Lexington, KY (US)

( * ) Notice: Subject to any disclaimer, the term of this patent is extended or adjusted under 35 U.S.C. 154(b) by 0 days.

(21) Appl. No.: 16/925,416

(22) Filed: Jul. 10, 2020

(65) Prior Publication Data

US 2020/0347314 A1 Nov. 5, 2020

Related U.S. Application Data

(62) Division of application No. 16/817,893, filed on Mar. 13, 2020.
(Continued)

(51) Int. Cl.
*C07C 5/10* (2006.01)
*G01N 30/92* (2006.01)
(Continued)

(52) U.S. Cl.
CPC .......... *C10M 105/02* (2013.01); *B01D 15/10* (2013.01); *C07C 5/10* (2013.01); *C07C 7/12* (2013.01);
(Continued)

(58) Field of Classification Search
CPC ... C07C 5/10; C07C 2523/46; C07C 2601/14; C07C 2521/18; G01N 30/92;
(Continued)

(56) References Cited

U.S. PATENT DOCUMENTS 2,530,774 A   11/1950   Kehe et al.
3,577,361 A   5/1971    Hammann et al.
(Continued)

FOREIGN PATENT DOCUMENTS

CN   102964199 B   12/2014
EP   0748863 A2   12/1996
(Continued)

OTHER PUBLICATIONS

International Search Report and Written Opinion issued in PCT application No. PCT/US2020/022559, dated Jul. 7, 2020.
(Continued)

*Primary Examiner* — Pamela H Weiss
(74) *Attorney, Agent, or Firm* — Benesch, Friedlander, Coplan & Aronoff LLP (57) ABSTRACT

A traction fluid comprising a blend of 2,3-dicyclohexyl-2,3-dimethylbutane (HAD) and 2,3-dicyclohexyl-2,3-dimethylbutane (iso-HAD) is found to have a lower viscosity at low temperatures when compared to a traction fluid having only HAD or only iso-HAD as a base fluid with no compromise to traction coefficient. The traction fluid may comprise additives. The traction fluid usually comprises HAD:iso-HAD between about 8:1 to about 1:3. Further, the HAD:iso-HAD traction fluid blend is produced by a method of simultaneous co-production of hydrogenated HAD and hydrogenated iso-HAD from an alpha styrene dimer and an iso-HAD precursor with a yield of about 90% in a method that does not require a purification step.

10 Claims, 4 Drawing Sheets

Related U.S. Application Data (60) Provisional application No. 62/817,732, filed on Mar. 13, 2019.

(51) Int. Cl.
  B01D 15/10 (2006.01)
  C07C 7/12 (2006.01)
  C10M 105/02 (2006.01)
  C10M 177/00 (2006.01)
  C10N 20/00 (2006.01)
  C10N 30/02 (2006.01)
  C10N 30/18 (2006.01)
  C10N 40/04 (2006.01)
  C10N 70/00 (2006.01)

(52) U.S. Cl.
  CPC ......... C10M 177/00 (2013.01); G01N 30/92 (2013.01); *C07C 2521/18* (2013.01); *C07C 2523/46* (2013.01); *C07C 2601/14* (2017.05); *C10M 2203/045* (2013.01); *C10N 2020/065* (2020.05); *C10N 2030/02* (2013.01); *C10N 2030/18* (2013.01); *C10N 2040/045* (2020.05); *C10N 2040/046* (2020.05); *C10N 2070/00* (2013.01)

(58) Field of Classification Search
  CPC ... B01D 15/10; C10M 105/02; C10M 177/00; C10M 2203/045; C10M 105/04; C10N 2020/065; C10N 2030/02; C10N 2030/18; C10N 2040/045; C10N 2040/046; C10N 2070/00; C10N 2020/02; C10N 2030/06
  See application file for complete search history.

(56) References Cited

U.S. PATENT DOCUMENTS

| | | | |
|---|---|---|---|
| 3,646,235 A | 2/1972 | Little et al. | |
| 3,677,970 A | 7/1972 | Miertzweiller et al. | |
| 3,925,217 A * | 12/1975 | Green | C10M 171/002 508/463 |
| 3,975,278 A | 8/1976 | Wygant | |
| 3,994,816 A | 11/1976 | Wygant | |
| 4,199,481 A | 4/1980 | Hall et al. | |
| 4,410,755 A | 10/1983 | Fisher | |
| 4,556,503 A * | 12/1985 | Tsubouchi | C10M 105/04 252/73 |
| 4,602,670 A | 7/1986 | Laemmle et al. | |
| 4,684,754 A | 8/1987 | Tsubouchi et al. | |
| 4,704,490 A | 11/1987 | Tsubouchi | |
| 4,830,767 A | 5/1989 | Waynick | |
| 4,889,649 A | 12/1989 | Murai et al. | |
| 4,975,215 A | 12/1990 | Kazuaki et al. | |
| 5,171,918 A | 12/1992 | Shubkin et al. | |
| 5,422,027 A | 6/1995 | Abe et al. | |
| 5,602,086 A | 2/1997 | Le et al. | |
| 5,627,147 A | 5/1997 | Hayakawa et al. | |
| 5,973,206 A | 10/1999 | Laitinen | |
| 6,001,780 A | 12/1999 | Ho et al. | |
| 6,191,330 B1 | 2/2001 | Matsuno et al. | |
| 6,239,085 B1 | 5/2001 | Slack | |
| 6,242,393 B1 | 6/2001 | Ishida et al. | |
| 6,319,879 B1 | 11/2001 | Yoshida et al. | |
| 6,320,088 B1 | 11/2001 | Matsuno et al. | |
| 6,372,696 B1 | 4/2002 | Tipton | |
| 6,488,898 B1 | 12/2002 | Lee et al. | |
| 6,730,640 B2 | 5/2004 | Sowerby et al. | |
| 6,846,782 B2 | 1/2005 | Calder | |
| 6,858,767 B1 | 2/2005 | Dimaio et al. | |
| 7,045,055 B2 | 5/2006 | Ziemer | |
| 7,402,715 B2 | 7/2008 | Yoshida et al. | |
| 7,425,524 B2 | 9/2008 | Haire | |
| 7,504,667 B2 | 3/2009 | Fujikura et al. | |
| 7,576,044 B2 | 8/2009 | Doner | |
| 7,585,823 B2 | 9/2009 | Sullivan et al. | |
| 7,629,303 B2 | 12/2009 | Hagemeister et al. | |
| 7,651,985 B2 | 1/2010 | Loh et al. | |
| 7,662,271 B2 | 2/2010 | Loh et al. | |
| 7,732,389 B2 | 6/2010 | Sullivan et al. | |
| 7,732,391 B1 | 6/2010 | Rosenbaum et al. | |
| 7,964,540 B2 | 6/2011 | Yoshida et al. | |
| 7,973,001 B2 | 7/2011 | Fujita et al. | |
| 8,143,200 B2 | 3/2012 | Vaughn et al. | |
| 8,227,392 B2 | 7/2012 | Wu et al. | |
| 8,247,358 B2 | 8/2012 | Lee | |
| 8,252,735 B2 | 8/2012 | Hagemeister et al. | |
| 8,399,390 B2 | 3/2013 | Wu et al. | |
| 8,476,205 B2 | 7/2013 | Lee | |
| 8,535,514 B2 | 9/2013 | Carey et al. | |
| 8,598,103 B2 | 12/2013 | Carey et al. | |
| 8,637,438 B2 | 1/2014 | Yamada | |
| 8,642,523 B2 | 2/2014 | Crouthamel | |
| 8,728,999 B2 | 5/2014 | Carey et al. | |
| 8,748,361 B2 | 6/2014 | Wu et al. | |
| 8,748,362 B2 | 6/2014 | Tellier et al. | |
| 8,759,267 B2 | 6/2014 | Tellier et al. | |
| 9,296,973 B2 | 3/2016 | Fu et al. | |
| 9,365,797 B2 | 6/2016 | Iwai | |
| 9,458,430 B2 | 10/2016 | Patil et al. | |
| 9,528,074 B2 | 12/2016 | Hogendoorn et al. | |
| 9,617,495 B2 | 4/2017 | Ghahary et al. | |
| 9,708,561 B2 | 7/2017 | Scherer et al. | |
| 9,719,046 B2 | 8/2017 | Beret et al. | |
| 9,725,672 B2 | 8/2017 | Fujita et al. | |
| 10,696,610 B2 * | 6/2020 | Rajule | C07C 5/10 |
| 2001/0010293 A1 | 8/2001 | Ishida et al. | |
| 2003/0207775 A1 | 11/2003 | Sullivan et al. | |
| 2004/0152607 A1 | 8/2004 | Chapaton et al. | |
| 2004/0152931 A1 | 8/2004 | Chapaton et al. | |
| 2004/0242441 A1 | 12/2004 | Chiu | |
| 2005/0121360 A1 | 6/2005 | Lange et al. | |
| 2005/0148478 A1 | 7/2005 | Ozbalik et al. | |
| 2006/0196807 A1 | 9/2006 | Rosenbaum | |
| 2006/0264339 A1 | 11/2006 | Devlin et al. | |
| 2007/0042915 A1 | 2/2007 | Yoshida et al. | |
| 2007/0087947 A1 | 4/2007 | Glasgow et al. | |
| 2008/0248983 A1 | 10/2008 | Goyal | |
| 2008/0274922 A1 | 11/2008 | Yagishita | |
| 2009/0088355 A1 | 4/2009 | Hee | |
| 2009/0298732 A1 | 12/2009 | Hoste | |
| 2010/0048434 A1 | 2/2010 | Hagemeister et al. | |
| 2011/0059877 A1 | 3/2011 | Obiols et al. | |
| 2012/0028857 A1 | 2/2012 | Lee | |
| 2013/0150626 A1 | 6/2013 | Mertens et al. | |
| 2014/0011384 A1 | 4/2014 | Givens | |
| 2014/0221260 A1 | 8/2014 | Herz | |
| 2014/0350038 A1 | 11/2014 | Reddy | |
| 2015/0353861 A1 | 12/2015 | Lee | |
| 2016/0230118 A1 | 8/2016 | Taylor et al. | |
| 2017/0044459 A1 | 2/2017 | Goyal et al. | |
| 2017/0183595 A1 | 6/2017 | Ng et al. | |
| 2017/0183596 A1 | 6/2017 | Ng et al. | |
| 2017/0183597 A1 | 6/2017 | Ng et al. | |
| 2019/0177249 A1 * | 6/2019 | Rajule | G01N 30/92 |

FOREIGN PATENT DOCUMENTS

| | | |
|---|---|---|
| EP | 1967753 A3 | 1/2010 |
| EP | 2937408 B2 | 1/2017 |
| JP | 60001354 B2 | 1/1985 |
| JP | 60096690 A | 5/1985 |
| JP | 60043392 B2 | 9/1985 |
| JP | 61051095 A | 3/1986 |
| JP | 63039986 A | 2/1988 |
| JP | 63213597 A | 9/1988 |
| JP | 1046494 B2 | 10/1989 |
| JP | 2018717 B2 | 4/1990 |
| JP | 2018719 B2 | 4/1990 |
| JP | 3080190 B2 | 12/1991 |
| JP | 4000518 B2 | 1/1992 |
| JP | 4001795 B2 | 1/1992 |
| JP | 4007734 B2 | 2/1992 |
| JP | 4034978 B2 | 6/1992 |

(56) References Cited

FOREIGN PATENT DOCUMENTS

| | | | |
|---|---|---|---|
| JP | 4068293 | B2 | 11/1992 |
| JP | 4075895 | B2 | 12/1992 |
| JP | 05-001292 | A | 1/1993 |
| JP | 5031914 | B2 | 5/1993 |
| JP | 5062918 | B2 | 9/1993 |
| JP | 6008425 | B2 | 2/1994 |
| JP | 6051874 | B2 | 7/1994 |
| JP | 6062984 | B2 | 8/1994 |
| JP | 6092593 | A | 11/1994 |
| JP | 7010992 | B2 | 2/1995 |
| JP | 7029946 | B2 | 4/1995 |
| JP | 7029947 | B2 | 4/1995 |
| JP | 7103387 | B2 | 11/1995 |
| JP | 02546796 | B2 | 10/1996 |
| JP | 02561758 | B2 | 12/1996 |
| JP | 02809448 | B2 | 10/1998 |
| JP | 02888734 | B2 | 5/1999 |
| JP | 2000087069 | B2 | 3/2000 |
| JP | 2001261589 | A | 9/2001 |
| JP | 2001342477 | A | 12/2001 |
| JP | 2002114714 | A | 4/2002 |
| JP | 03599231 | B2 | 12/2004 |
| JP | 2005170903 | A | 6/2005 |
| JP | 2007146017 | A | 6/2007 |
| JP | 04044225 | B2 | 2/2008 |
| JP | 04145999 | B2 | 9/2008 |
| JP | 04166309 | B2 | 10/2008 |
| JP | 04184767 | B2 | 11/2008 |
| JP | 2009-067961 | A | 4/2009 |
| JP | 04354070 | B2 | 10/2009 |
| JP | 04377687 | B2 | 12/2009 |
| JP | 04422286 | B2 | 2/2010 |
| JP | 04448709 | B2 | 4/2010 |
| JP | 04456718 | B2 | 4/2010 |
| JP | 04521275 | B2 | 8/2010 |
| JP | 04560157 | B2 | 10/2010 |
| JP | 04562906 | B2 | 10/2010 |
| JP | 04675779 | B2 | 4/2011 |
| JP | 04700288 | B2 | 6/2011 |
| JP | 04792171 | B2 | 10/2011 |
| JP | 04891469 | B2 | 3/2012 |
| JP | 04938250 | B2 | 5/2012 |
| JP | 04999320 | B2 | 8/2012 |
| JP | 05431657 | B2 | 3/2014 |
| JP | 2015172135 | A | 10/2015 |
| JP | 05816497 | B2 | 11/2015 |
| JP | 05872946 | B2 | 3/2016 |
| JP | 2016030803 | A | 3/2016 |
| JP | 06182480 | B2 | 8/2017 |
| JP | 2017160407 | A | 9/2017 |
| JP | 2019131637 | A | 8/2019 |
| WO | 2011094562 | A1 | 8/2011 |
| WO | 2011094566 | A1 | 8/2011 |

OTHER PUBLICATIONS

B. Chaudhuri et al., Some Novel Aspects of the Dimerization of α-Methylstyrene with Acidic Ion-Exchange Resins, Clays and other Acidic Materials as Catalysts, Ind. Eng. Chem. Res., vol. 28, No. 12: 1989, pp. 1757-1763.
T. Tsubouchi, et al., Quantitative Correlation Between Molecular Structures of Traction Fluids and Their Traction Properties (Part 1): Influence of Alkylene Chain, Japanese Journal of Tribology, vol. 38, No. 3: 1993, pp. 403-410.
T. Tsubouchi, et al., Optimisation of Molecular Structure for Traction Fluids, Lubrication Scienc, ISSN 0954-0075: Aug. 2004, pp. 393-403.
International Search Report and Written Opinion issued in PCT application PCT/2018/064710, dated Feb. 21, 2019.
International Search Report and Written Opinion in International Application No. PCT/US2019/020880, dated Jun. 13, 2019 (10 pages).
B. Chaudhuri et al., Some Novel Aspects of the Dimerization of a-Methylstyrene with Acidic Ion-Exchange Resins, Clays and other Acidic Materials as Catalysts, Ind. Eng. Chem. Res., vol. 28, No. 12: 1989, pp. 1757-1763.

* cited by examiner

TRACTION FLUID WITH IMPROVED LOW TEMPERATURE PROPERTIES

PRIORITY DATA

This application is a divisional of U.S. application Ser. No. 16/817,893 filed Mar. 13, 2020 which claims priority to U.S. Provisional Patent Application No. 62/817,732, filed Mar. 13, 2019, herein incorporated by reference in its entirety.

FIELD OF INVENTION

The present disclosure generally relates to a traction fluid blend for an IVT with improved viscosity at low temperatures. Also disclosed, a method of simultaneously hydrogenating a blend of molecules to produce a traction fluid base oil.

BACKGROUND

Traction fluids rely on its high shear strength to provide torque transmission in devices like continuous variable transmission (CVT) or infinite variable transmission (IVT). Such transmission allows seamless integration with internal combustion engine for optimal engine performance and maximum fuel efficiency. In the year 1999, toroidal continuous variable transmission (T-CVT) cars were introduced in the market and the traction fluid used for T-CVT requires high level of performance in terms of high traction coefficient and low temperature fluidity of the fluid.

SUMMARY

The surprising and non-obvious discovery that iso-HAD, a molecule that by itself is solidified at low temperatures can improve the fluidity of a HAD:iso-HAD blend at low temperatures will now be described.

A traction fluid that provides improved fluidity as a low temperature is a blend of:

Formula I

Formula II and one or more additives.

The traction fluids that are a blend have improved properties of lower viscosities at low temperatures with no effect on overall traction coefficient of the fluid.

Methods of making a traction fluid blend stock are also provided. The methods have the advantage of simultaneously hydrogenating a HAD precursor and an iso-HAD precursor in a reaction vessel such that the reaction product requires no purification and instantly contains HAD and iso-HAD in a preferred mix ratio. The reaction product that is a blend of HAD and iso-HAD that may then be combined with additives to form a finished traction fluid.

In the methods, the HAD precursor serves not only as reactant but also solvent for the iso-HAD precursor.

Other fluids, methods, features and/or advantages is, or will become, apparent upon examination of the following FIGs and detailed description. It is intended that all such additional fluids, methods, features, and advantages be included within this description and be protected by the accompanying claims.

BRIEF DESCRIPTION OF THE DRAWINGS

In the accompanying figures, chemical formulas, chemical structures, and experimental data are given that, together with the detailed description provided below, describe example embodiments.

DETAILED DESCRIPTION

The traction fluid blend will be described in detail.

HAD

Tsubouchi et al. (*Lubrication Science* 2004, 16(4), 393-403) reported parameters for designing molecular structure with high traction coefficient including high molecular stiffness, large size, short alkylene chain length, high melting point and low molecular polarity for getting good traction coefficient. The industry uses specially designed traction fluid such as hydrogenated alpha dimethyl styrene (HAD), which has excellent traction coefficient and low temperature viscosity-key performance parameters including: Melting point −30° C., boiling point 112° C. (0.7 mm of Hg). The traction coefficient of HAD is reported as 0.058 at 140° C., with slide to roll ratio of 5% and maximum Hertz pressure of 1.1 GPa (*Japanese Journal of Tribology* Vol 38, 3, 1993). The chemical structure of HAD (CAS 38970-72-8; 2,4-dicyclohexyl-2-methylpentane) is presented in Formula I:

Formula I

IsoHAD

The chemical structure of isoHAD (CAS 5171-88-0; 2,3-dicyclohexyl-2,3-dimethylbutane) is presented in Formula II:

Formula II

HAD/isoHAD Blends

Table 1 compares properties of Formula I and Formula II.

|  | Formula I (HAD) | Formula II (isoHAD) |
| --- | --- | --- |
| Kinematic Viscosity @ 40° C. (cSt) | 19.95 | 28.87 |
| Kinematic Viscosity @ 100° C. (cSt) | 3.56 | 4.7 |
| Viscosity Index | 16 | 65 |
| Brookfield viscosity @−30° C. (cP) | 29,000 | Frozen |
| Pour Point (° C.) | −30 | −12 |
| Traction coefficient @ 90 C., 5% SRR, 1.25 GPa | 0.0995 | 0.1001 |

Additives

The traction fluid may comprise, in addition to a blend of Formula I and II, additives. Any additive that may improve the properties or functioning of the traction fluid may be added. The traction fluid may also comprise additives in an amount greater than about 0.01 (w/w) % and less than about 20 (w/w) %. The amount of any one additive may be in an amount between 0.01 (w/w) % and less than about 20 (w/w) %. If more than one additive is added to the formulation, the total amount of additives present may be in an amount from 0.01 (w/w) % and less than about 20 (w/w) %. Alternatively, the amount 0.01 (w/w) % and less than about 20 (w/w) % may refer to the each additive present in the traction fluid.

The additive may comprise an antifoaming agent that may be present in an amount of about 0.1 (w/w) %. The antifoaming agent may be a mixture of organic acid ester and siloxane or a silicone based fluid. The traction fluid may contain one, two or more than two anti-foaming agents. The antifoaming agent may comprise any appropriate defoamer.

The traction fluid may also comprise a viscosity modifier. The viscosity modifier may be present in an amount between 0.1 (w/w) % to 10 (w/w) % depending on target viscosity of the finished fluid.

The traction fluid may include additional additives such as an additive package including antioxidant agents, antiwear agents, extreme pressure agents, detergents, dispersants, antifoamer, anti-rust agents, friction modifiers, corrosion inhibitors, viscosity modifiers. The additive package may be added in an amount greater than about 0.01 (w/w) % and less than about 20 (w/w) %. The additive amount may also be described by any single digit found in the range between about 0.01 (w/w) % and less than about 20 (w/w) %, such as 5 (w/w) % or 7.8 (w/w) %. The additive may comprise, may consist essentially of or consist of a single ingredient, such as one de-foaming agent. Alternatively, the additive may comprise, may consist essentially of or consist of a commercially available additive package. The additive may comprise, may consist essentially of or consist of a viscosity modifier. The additive may comprise, may consist essentially of or consist of a combination of a defoamer, viscosity modifier and a transmission additive package.

The traction fluid may further optionally comprise a transmission additive package. The transmission additive package may be added in an amount greater than about 0.01 (w/w) % and less than about 20 (w/w) %. The additive amount may also be described by any single digit found in the range between about 0.01 (w/w) % and less than about 20 (w/w) %, such as 5.7 (w/w) % or 9.0 (w/w) %.

A traction fluid may comprise a blend of the molecule of Formula I:

Formula I and
the molecule of Formula II:

Formula II

The traction fluid that is a blend of Formula I and Formula II may also contain one or more additives selected from the group consisting of: anti-foaming agents, antioxidant agents, antiwear agents, extreme pressure agents, detergents, dispersants, anti-rust agents, friction modifiers, corrosion inhibitors, and viscosity modifiers.

All of the additives considered together may be present in an amount between about 0.01 (w/w) % and about 20 (w/w) % where the blend of Formula I and Formula II is present in an amount between about 80 (w/w) % and 99.99 (w/w) %.

The traction fluid may include one additive that is a defoaming agent in an amount of about 0.1 (w/w) %, a second additive that is a viscosity modifier in an amount of about 2 (w/w) %, and a third additive is a transmission additive package in an amount of about 5.7 (w/w) %. The additive may comprise, may consist essentially of or consist of a defoaming agent, a viscosity modifier and a transmission additive package.

The traction fluid may contain a blend of Formula I and Formula II in an amount between about 92 (w/w) % and about 94 (w/w) %.

The traction fluid may be described as follows. The amount of Formula I and Formula II relative to each other by may be defined by a mix ratio. The mix ratio, HAD:iso-HAD represents the amount of HAD (w/w) % relative to the isoHAD (w/w) %. Most preferably the mix ratio of HAD:iso-HAD is between 8:1 and 1:3. Even more preferably the mix ratio of HAD:isoHAD is between 1:1 and 1:3.

The traction fluids that are a blend of Formula I (HAD) and Formula II (iso-HAD) are characterized by: a viscosity that is lower than the viscosity of a traction fluid comprising Formula I or II as a base fluid alone; and/or a traction coefficient approximately equivalent to a traction fluid comprising Formula I or II as a base fluid alone.

The traction fluids that are a blend of Formula I and Formula II are characterized by: the viscosity of the a traction fluid blend being about 25 to 30% lower than the viscosity of a traction fluid comprising Formula I as a base fluid alone. In addition, the traction coefficient of the traction fluid blend is generally within about 1% of the traction coefficient of a traction fluid comprising Formula I as a base fluid alone. That is, the variation in the traction coefficient as measured does not vary from the traction coefficient of a traction fluid blend comprising only Formula I by greater than 1% of the traction coefficient value. Similarly, when a traction fluid HAD:isoHAD blend is compared to a traction fluid comprising HAD (Formula I), the variation in viscosity of the blend as measured by Brookfield viscosity @–30° C. (cP) does not vary by more than 30% when compared to fluids with HAD alone as base fluid. The traction fluids comprising only Formula II has un-measurable Brookfield viscosity @–30° C. as it freezes at that temperature, while its traction coefficient is slightly higher than the traction fluid of a blend of Formula I and Formula II.

Co-Synthesis of HAD and isoHAD

Inventors have previously disclosed a novel and scalable method for production of HAD from an alpha methyl styrene in U.S. patent application Ser. No. 16/214,867, filed Dec. 10, 2018.

Now a procedure for simultaneous co-hydrogenation of alpha dimethyl styrene dimer and an iso-HAD precursor that is scalable, economical, and safe will be described in detail. These procedures result in routinely greater than a 90% yield of a co-product.

The process can be summarized as follows:

Molecular Weight: 236.36
HAD precursor
Fomula III

Molecular Weight: 238.37
iso-HAD precursor
Formula IV

Molecular Weight: 250.47
HAD
Formula I

Molecular Weight: 250.47
iso-HAD
Formula II

The methods of co-synthesis of HAD and iso-HAD require no purification step.

The methods of co-synthesis also provide a convenient method of preparing an iso-HAD precursor for hydrogenation because the HAD precursor, while being a reactant is additionally a solvent for the iso-HAD precursor.

The terms co-synthesis, co-production, co-products all refer to the fact that a HAD precursor and an iso-HAD precursor are added to a reactant vessel and both undergo a hydrogenation reaction simultaneously in the same reactant vessel.

The methods include adding to a Haste alloy reactor, with turbine impeller, under nitrogen a catalyst comprising Ru/C or Rh/C, an alpha dimethyl styrene dimer, and an iso-HAD precursor to form a reaction mixture. The reaction mixture is then heated under pressure until hydrogenation of the alpha dimethyl styrene dimer and of the iso-HAD precursor is complete. To recover the hydrogenated alpha dimethyl styrene dimer and iso-HAD, the reaction mixture is filtered through a celite bed under nitrogen to remove the catalyst. The catalyst may be recovered from the celite bed and recycled for use again in the method. This method of production is solventless or adds an amount of a protic solvent such as isopropyl alcohol. The reaction time varies from about 6 hours to 22 hours. The reaction time can be reduced by increasing the temperature and pressure.

The hydrogenation reaction may be monitored for completion by performing thin layer chromatography on a sample of the reaction mixture. The reaction is complete when hydrogen consumption ceases. Likewise, a sample of the reaction mixture may be analyzed by the absence of an aromatic peak in a nuclear magnetic resonance (NMR) spectra. Gas chromatograph mass spectrometry (GCMS) or any other technique may also be used to evaluate the completeness of the hydrogenation reaction.

Thus provided is a method for co-preparing HAD and iso-HAD comprising: adding to a reactor under nitrogen a catalyst comprising Ru/C or Rh/C; adding alpha dimethyl styrene dimer and an iso-HAD precursor to the reactor thereby forming a catalyst, alpha dimethyl styrene dimer, iso-HAD precursor reaction mixture; heating the reaction mixture under pressure until hydrogenation of the alpha dimethyl styrene dimer and the iso-HAD precursor is complete; and filtering the reaction mixture through a celite bed under nitrogen thereby obtaining a hydrogenated alpha dimethyl styrene dimer (HAD) and a hydrogenated iso-HAD (iso-HAD) co-product.

The reaction of the method of can proceed for about 6 to about 22 hours until completion. The heating of the method may include beginning with the formation of the reaction mixture in the reactor at ambient temperature and raising the temperature of the reaction mixture to about 110° C. or to about 125° C. until completion of the reaction. The reaction mixture in the reactor may be under a pressure of between about 14 and about 15 Kg/cm$^2$. The reaction mixture in the reactor may be constantly stirred.

The method may also include a step of monitoring reaction completeness by testing the filtered hydrogenated alpha dimethyl styrene dimer product by nuclear magnetic resonance spectroscopy.

The method includes reaction conditions where the alpha methyl styrene dimer and iso-HAD precursor are added to the reaction mixture in equal amounts or where the ratio of alpha methyl styrene dimer:iso-HAD precursor are added to the reaction mixture is a ratio of between about 8:1 to about 1:3.

EXAMPLES

Example 1: Traction Fluid Blends of HAD and isoHAD

Compositions that blend of HAD (Formula I) and iso-HAD (Formula II) were made and are summarized in Table 2:

| Fluid | A | B | C | D | E | F |
|---|---|---|---|---|---|---|
| HAD:isoHAD |  | 8:1 | 3:1 | 2:1 | 1:1 | 1:2 |
| HAD | 92.2 | 82.2 | 69.5 | 62.13 | 46.78 | 31.23 |
| iso-HAD |  | 10 | 23.4 | 31.07 | 46.78 | 62.47 |
| VM | 2 | 2 | 1.3 | 1 | 0.64 | 0.5 |
| DI | 5.7 | 5.7 | 5.7 | 5.7 | 5.7 | 5.7 |
| Defoamers | 0.1 | 0.1 | 0.1 | 0.1 | 0.1 | 0.1 |
| Total | 100 | 100 | 100 | 100 | 100 | 100 |
| KV100 (cSt) | 4.88 | 4.99 | 4.79 | 4.75 | 4.74 | 4.89 |
| KV40 (cSt) | 26.73 | 27.29 | 27.13 | 27.71 | 27.78 | 29.24 |

-continued

| | | | | | | |
|---|---|---|---|---|---|---|
| Traction Coef. | 0.0942 | | | | 0.0948 | 0.0946 |
| BF-30C (cP) | 26,200 | 24,800 | 24,000 | 22,600 | 19,900 | 19,500 |
| BF-40C (cP) | 228,000 | | | | 164,800 | 162,500 |

| Fluid | G | H | I | J | K |
|---|---|---|---|---|---|
| HAD:isoHAD | 1:3 | 1:4 | 1:5 | 1:6 | |
| HAD | 23.56 | 18.85 | 15.7 | 11.72 | |
| iso-HAD | 70.64 | 75.35 | 78.5 | 82.03 | 94.2 |
| VM | | | | 0.45 | |
| DI | 5.7 | 5.7 | 5.7 | 5.7 | 5.7 |
| Defoamers | 0.1 | 0.1 | 0.1 | 0.1 | 0.1 |
| Total | 100 | 100 | 100 | 100 | 100 |
| KV100 (cSt) | 4.76 | 4.84 | 4.88 | 5.23 | 5.15 |
| KV40 (cSt) | 28.7 | 29.37 | 29.94 | 31.68 | 32.11 |
| Traction Coef. | 0.0947 | | 0.0949 | | 0.095 |
| BF-30C (cP) | 19,150 | 19,100 | 20,300 | frozen | frozen |
| BF-40C (cP) | 158,200 | frozen | frozen | frozen | frozen |

In Table 2, the following abbreviations are used: HAD refers to Formula I; iso-HAD refers to Formula II, DI refers to a transmission additive package; VM refers to a viscosity modifier; KV100 (cSt) and KV40 (cSt) refer to Kinematic Viscosity @ 100° C. and 40° C., respectively; Traction Coef. refers to Traction Coefficient @ 90° C., 5% SRR, 1.25 GPa; BF-30 (cP) and BF-40 (cP) refer Brookfield viscosity @-30° C. and -40° C. respectively.

Figure 1:
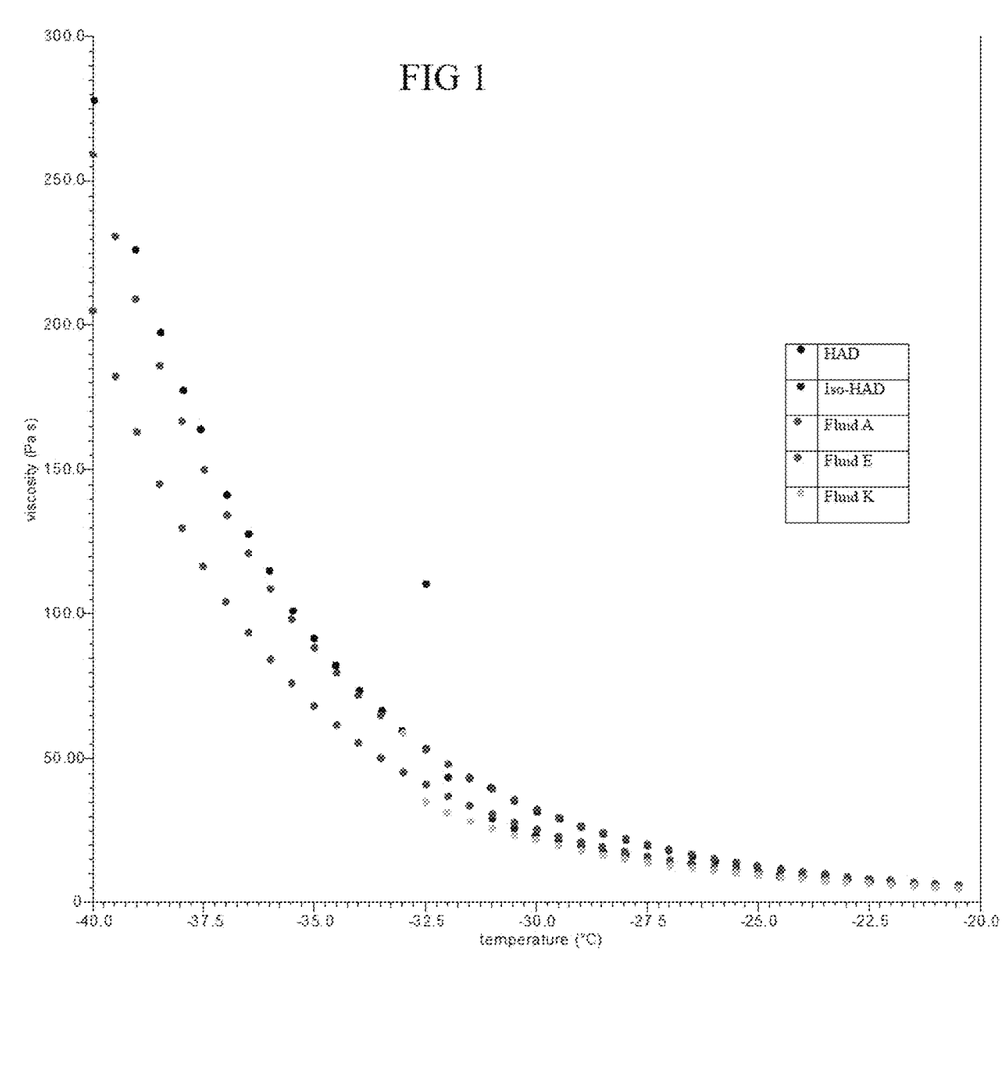
FIG. 1 is a graph demonstrating viscosity changes as temperature changes for fluids of different compositions.

Referring now to FIG. 1, the viscosity of Fluids A, E and K, a fluid that is 100% iso-HAD (no additives) and a fluid that is 100% HAD (no additives) as a function of temperature are shown. Fluid E, with a mix ratio of 1:1 has a lower viscosity than fluid A and improved viscosity over Fluid K, which is frozen at lower temperatures.

As can be seen in Table 2, the compositions contain the additives transmission additive package, defoamers and viscosity modifiers in amounts up to about 7.8 (w/w) % total. The amount of Formula I and Formula II are varied. The mix ratio of HAD:iso-HAD characterizes the amount of Formula I and Formula II to each other in the traction fluid composition. The traction coefficient were measured at 90° C. and pressure of 1.25 GPa under 5% slide to roll ratio. For Brookfield viscosity, 'frozen' indicates the viscosity is too high to measure when fluid freezes.

As can be seen in the Table 2, the traction coefficient increases slightly with increasing amounts of Formula II (iso-HAD) in the blend (compare traction coefficient of Fluid A (100% HAD) to fluids B-K). Not wishing to be bound by theory, but this is likely due to the fact that Formula I (HAD) has lower traction coefficient than Formula II (see Table I). However, Brookfield viscosity at -30° C. decreases with increasing concentration of iso-HAD and reaches a plateau at fluids E through I. The Brookfield viscosity at -30° C. increases at mix ratio of 1:6. The Brookfield viscosity at -40° C. increases at mix ratio of 1:4. Most preferably, the formulations of Fluid E, F, and G, with a mix ratio of HAD:iso-HAD between 1:1 to 1:3 provide the optimal balance between performance (traction coefficient) and viscosity (Brookfield viscosity).

The traction fluids from blends of HAD and iso-HAD (Fluid B to J in Table 2) have lower low temperature viscosity than the traction fluids with HAD only (Fluid A) or iso-HAD only (Fluid K). Not wishing to be bound by theory, the reason behind this phenomena may be due to the fact that the viscosity of iso-HAD is actually lower than the viscosity of HAD before iso-HAD freezes, as it is demonstrated by rheometer test in FIG. 1 where sudden viscosity increase indicates freezing of the fluid.

The traction fluids from blend of HAD and iso-HAD have lower freezing point than iso-HAD while have lower viscosity than HAD.

Example 2: Co-Synthesis of HAD and isoHAD

In a one-liter Haste alloy reactor, with turbine impeller, a catalyst according to Table 3 was added. To the catalyst, isopropyl alcohol was added under nitrogen, in some of the examples. To the resultant catalytic solution, alpha dimethyl styrene dimer (AMS) and iso-HAD precursor was added. The reaction mixture was stirred with a stirrer at a constant rate of 700 RPM. The reaction mixture was heated to the temperature and pressure indicated in Table 3. Completion of the reaction was monitored by thin layer chromatography or NMR and when no more hydrogen consumption was indicated, the reaction mixture was filtered through a celite bed under nitrogen. The product was also analyzed by nuclear magnetic resonance (NMR). The yield was about 90-92%.

The results are shown in Table 3:

TABLE 3

Figure 2A:
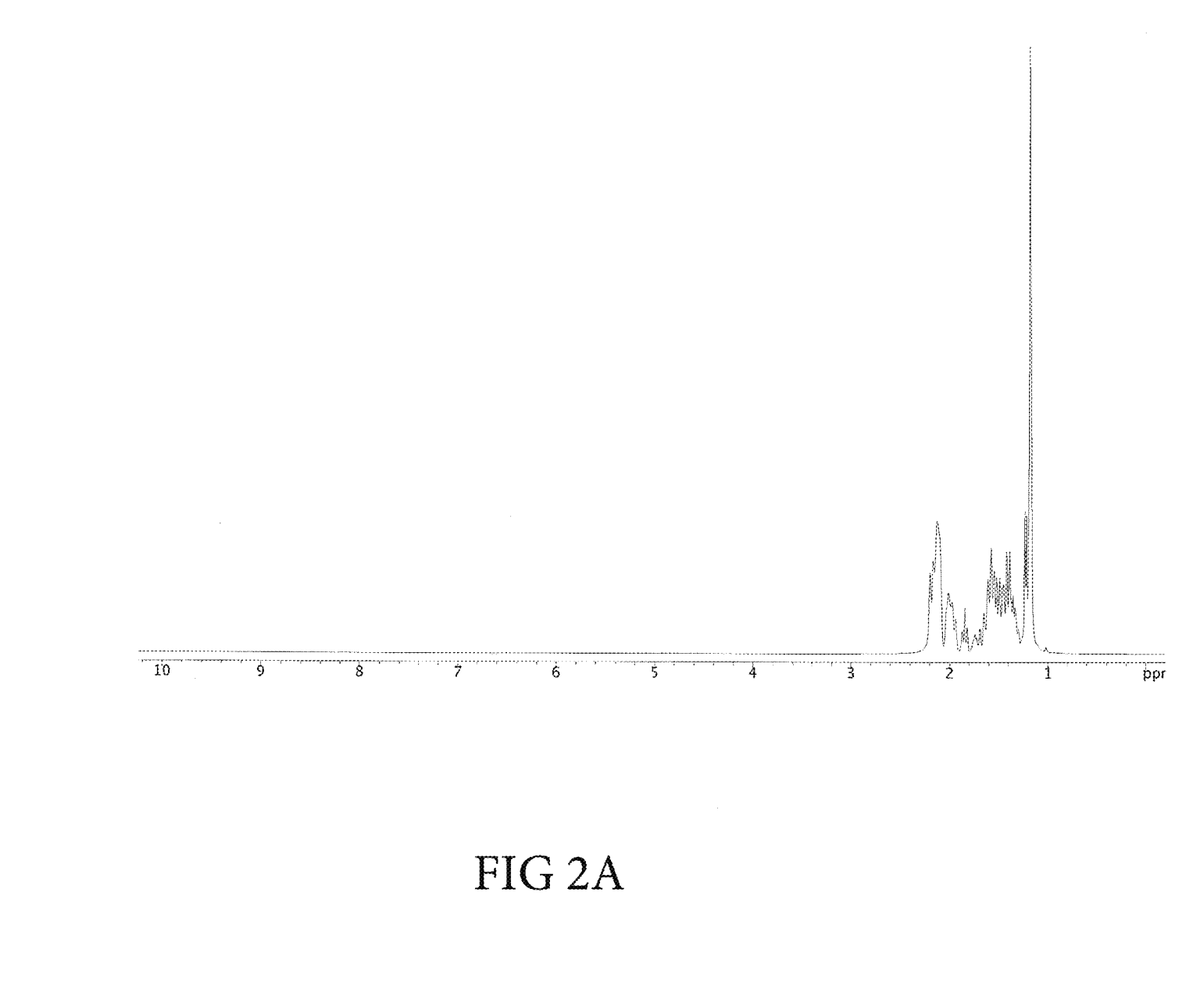
FIG. 2A-C shows the NMR spectra for co-produced hydrogenated alpha dimethyl styrene dimer and hydrogenated iso-HAD prepared according to the methods of the present disclosure.

| AMS dimer (g) | Iso-HAD Precursor (g) | Solvent | Catalyst (Loading wt %) | Temp (° C.) | Pressure (Kg/cm2) | Reaction time (h) | Remarks |
|---|---|---|---|---|---|---|---|
| 50 | 50 | IPA (250 ml) | 10% Rh/C (5 wt % of the Input feed) | 100-110° C. | 14-15 | 6 | NMR shows absence of aromatic peak See FIG. 2A |
| 50 | 50 | IPA (250 ml) | 10% Ru/C (5 wt % of the Input feed) | 100-110° C. | 14-15 | 7.5 | NMR shows absence of aromatic peak |
| 50 | 50 | IPA (250 ml) | 5% Ru/C (1 wt % of the Input feed) | 100-110° C. | 14-15 | 11.5 | NMR shows absence of aromatic peak |

TABLE 3-continued

Figure 2B:
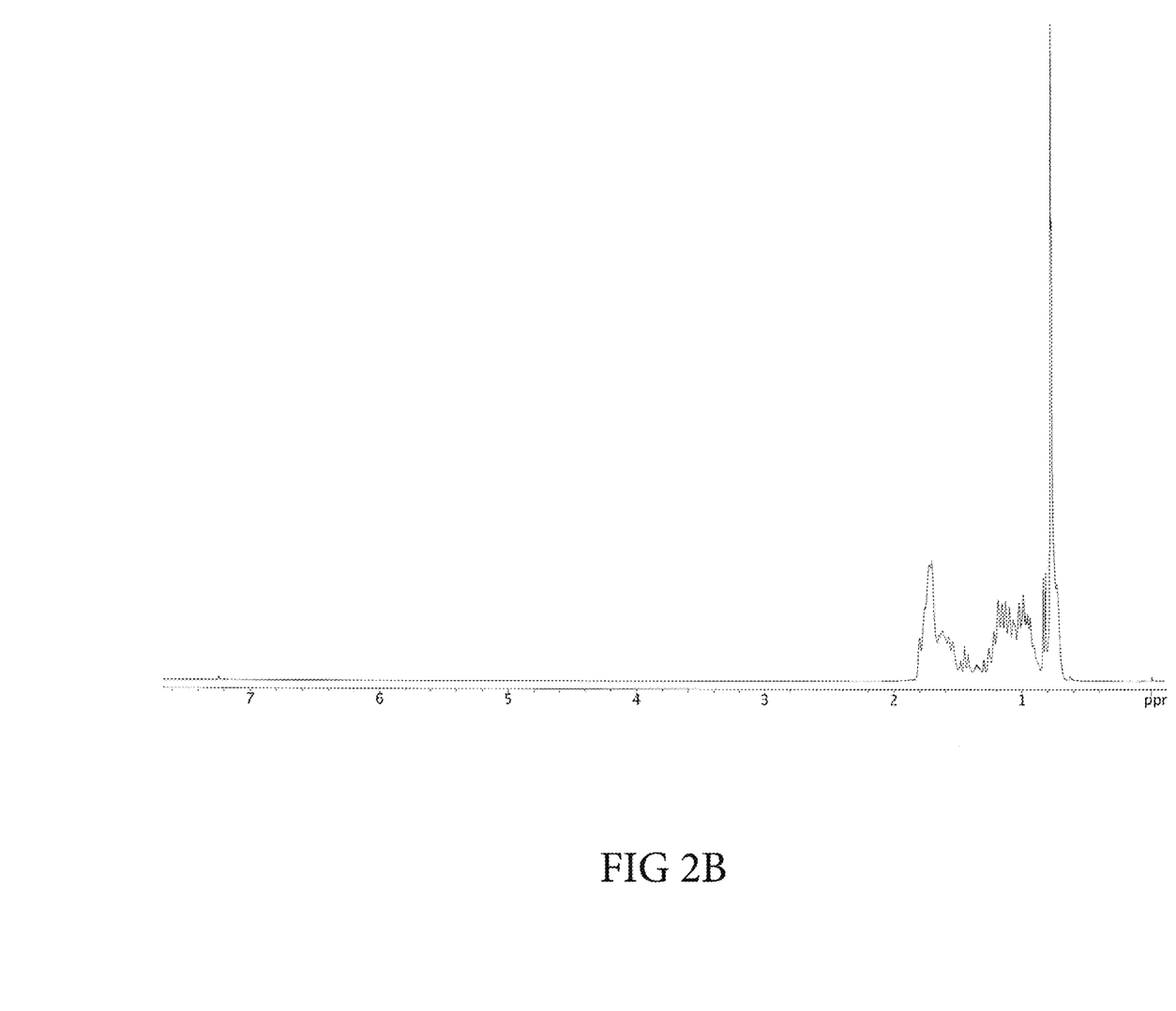
Figure 2C:
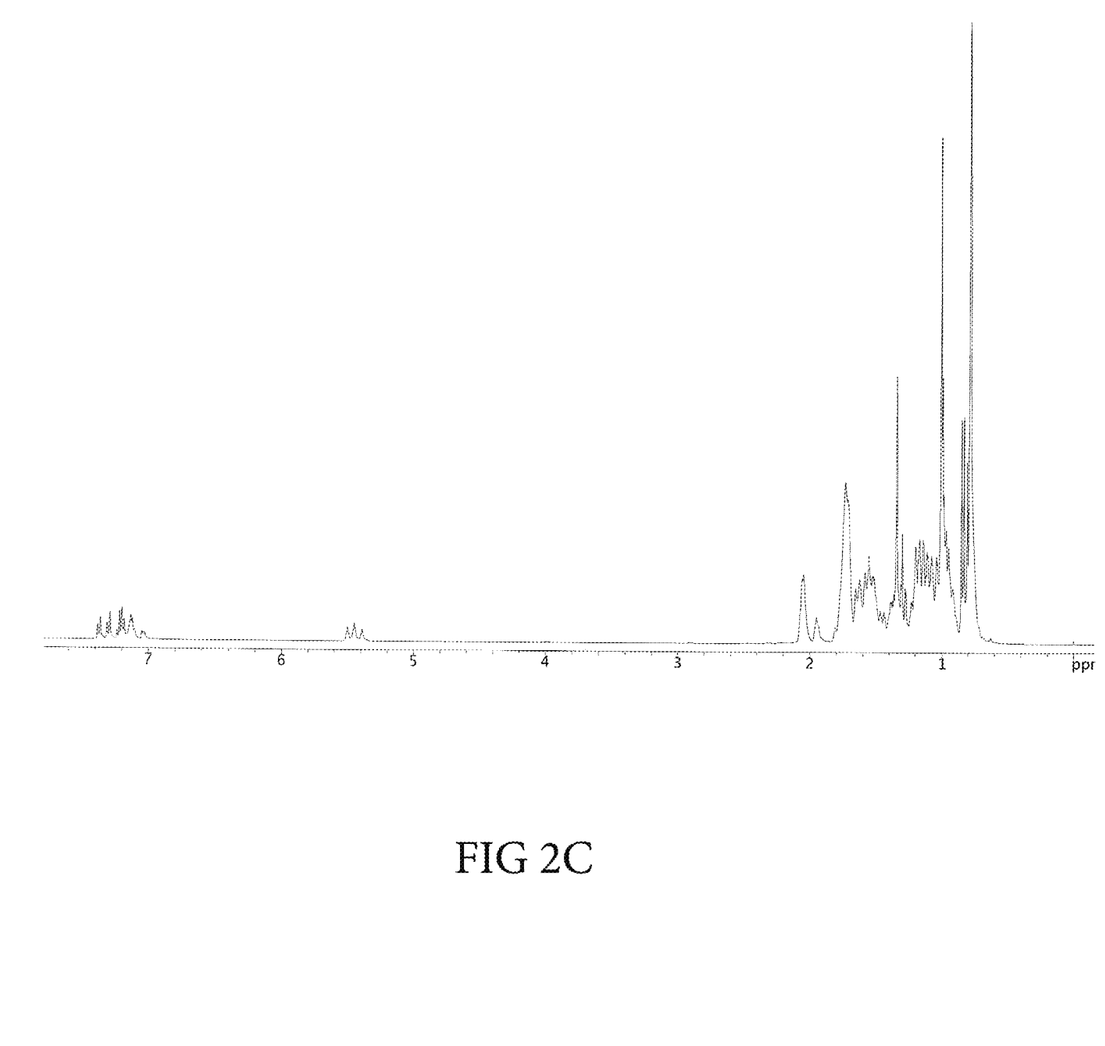

| AMS dimer (g) | Iso-HAD Precursor (g) | Solvent | Catalyst (Loading wt %) | Temp (° C.) | Pressure (Kg/cm2) | Reaction time (h) | Remarks |
|---|---|---|---|---|---|---|---|
| 100 | 100 | — | 5% Ru/C (2 wt % of the Input feed) | 120-125° C. | 14-15 | 22 | NMR shows absence of aromatic peak See FIG. 2B |
| 75 | 75 | — | 5% Ru/C (1 wt % of the Input feed) | 120-125° C. | 14-15 | >22 | NMR show presence of aromatic peaks (Incomplete reaction) See FIG. 2C |

As evidenced by the NMR spectra, FIGS. 2A and 2B, the absence of aromatic peaks indicates completion of the hydrogenation reaction. In contrast, FIG. 2C demonstrates an incomplete reaction. The incomplete reaction of FIG. 2C may be completed by increasing temperature and pressure. Increasing temperature and pressure may also be used to reduce the reaction time.

In the fourth reaction, the HAD precursor acts as solvent and reactant. The HAD precursor is in a liquid state while the iso-HAD precursor is in a solid physical state and a slurry of iso-HAD and HAD was first mixed and then added to the reaction vessel.

Hydrogenation reactions are generally carried out in a polar solvent. Here, the HAD precursor may act as solvent for the iso-HAD. Thus the HAD provides a polar medium, but as it is also a reactant and as the reaction progresses, more HAD is hydrogenated and therefore not able to perform as polar solvent. Without wishing to be bound by theory, it is speculated this is why the reaction is faster in the beginning but as the reaction mixture slowly turns non polar in nature, the reaction slows and thus a reaction time such as 22 hours may be necessary.

Certain embodiments have been described in the form of examples. It is impossible to depict every potential application. Thus, while the embodiments are described in considerable detail, it is not the intention to restrict or in any way limit the scope of the appended claims to such detail, or to any particular embodiment.

To the extent that the term "includes" or "including" is used in the specification or the claims, it is intended to be inclusive in a manner similar to the term "comprising" as that term is interpreted when employed as a transitional word in a claim. Furthermore, to the extent that the term "or" is employed (e.g., A or B) it is intended to mean "A or B or both." When "only A or B but not both" is intended, then the term "only A or B but not both" will be employed. Thus, use of the term "or" herein is the inclusive, and not the exclusive use. As used in the specification and the claims, the singular forms "a," "an," and "the" include the plural. Finally, where the term "about" is used in conjunction with a number, it is intended to include ±10% of the number. For example, "about 10" may mean from 9 to 11. The term HAD may be used to refer to a hydrogenated alpha dimethyl styrene dimer or hydrogenated dimers of alpha olefins, or any other term referring to the FIGs shown in Formula I or defined as HAD.

As stated above, while the present application has been illustrated by the description of embodiments, and while the embodiments have been described in considerable detail, it is not the intention to restrict or in any way limit the scope of the appended claims to such detail. Additional advantages and modifications will readily appear to those skilled in the art, having the benefit of this application. Therefore, the application, in its broader aspects, is not limited to the specific details and illustrative examples shown. Departures may be made from such details and examples without departing from the spirit or scope of the general inventive concept.

The invention claimed is:

1. A method for co-preparing HAD and iso-HAD comprising:
adding to a reactor under nitrogen a catalyst comprising Ru/C or Rh/C;
adding alpha dimethyl styrene dimer and iso-HAD precursor to the reactor thereby forming a catalyst, alpha dimethyl styrene dimer, and iso-HAD precursor reaction mixture;
heating the reaction mixture under pressure until hydrogenation of the alpha dimethyl styrene dimer and the iso-HAD precursor is complete; and
filtering the reaction mixture through a celite bed under nitrogen to remove the catalyst and thereby obtaining a hydrogenated alpha dimethyl styrene dimer (HAD) and a hydrogenated iso-HAD (iso-HAD) co-products.

2. The method of claim 1, wherein the alpha dimethyl styrene dimer and iso-HAD precursor are mixed with each other prior to addition to the reactor and the alpha dimethyl styrene dimer is both reactant and solvent for the iso-HAD precursor.

3. The method of claim 2, further comprising recovering of the catalyst from the celite bed after the filtration step and reusing the catalyst in subsequent reactions.

4. The method of claim 2, wherein the reaction proceeds for about 6 to about 22 hours until completion.

5. The method of claim 2, the heating processing further characterized by beginning with the formation of the reaction mixture in the reactor at ambient temperature and raising the temperature of the reaction mixture to about 110° C. to about 125° C.

6. The method of claim 2, wherein the reaction mixture in the reactor is under a pressure of between about 14 Kg/cm$^2$ and about 15 Kg/cm$^2$.

7. The method of claim 2, wherein the reaction mixture in the reactor is constantly stirred.

8. The method of claim 2, further comprising the step of monitoring reaction completeness by testing the filtered hydrogenated HAD and hydrogenated iso-HAD product by nuclear magnetic resonance.

9. The method of claim 2, wherein the alpha methyl styrene dimer and iso-HAD precursor are added to the reaction in equal amounts.

10. The method of claim 2, wherein the ratio of alpha methyl styrene dimer:iso-HAD precursor are added to the reaction is a ratio of between about 8:1 to about 1:3.

* * * * *